US012631775B2

(12) United States Patent
    Kosuge

(10) Patent No.:    US 12,631,775 B2
(45) Date of Patent:       May 19, 2026

(54) RADIATION IMAGING APPARATUS AND RADIATION IMAGING SYSTEM

(71) Applicant: CANON KABUSHIKI KAISHA, Tokyo (JP)

(72) Inventor: Asato Kosuge, Kanagawa (JP)

(73) Assignee: Canon Kabushiki Kaisha, Tokyo (JP)

( * ) Notice:    Subject to any disclaimer, the term of this patent is extended or adjusted under 35 U.S.C. 154(b) by 34 days.

(21) Appl. No.: 18/423,051

(22) Filed:    Jan. 25, 2024

(65)                Prior Publication Data

US 2024/0280713 A1      Aug. 22, 2024

(30)        Foreign Application Priority Data

Jan. 27, 2023    (JP) ................................ 2023-010854

(51) Int. Cl.
    *G01T 1/24*        (2006.01)
    *A61B 6/00*        (2006.01)
    *A61B 6/42*        (2024.01)
    *G01T 1/20*        (2006.01)
(52) U.S. Cl.
    CPC ........ *G01T 1/20184* (2020.05); *A61B 6/4233* (2013.01); *A61B 6/542* (2013.01)
(58) Field of Classification Search
    CPC ....... G01T 1/247; G01T 1/20184; G01T 1/17;
    H04N 23/30; H04N 25/30; H04N 25/40;
    H04N 25/626; H04N 25/78; H04N 5/32;
    A61B 6/4233; A61B 6/465; A61B 6/54
    See application file for complete search history.

(56)                References Cited

U.S. PATENT DOCUMENTS

2015/0182182 A1     7/2015  Tajima
    2018/0295294 A1    10/2018  Kameshima
    2018/0321397 A1    11/2018  Kawanabe
    2019/0146103 A1*    5/2019  Ofuji ...................... H04N 23/30
                                                250/370.08

FOREIGN PATENT DOCUMENTS

JP          2016025465 A     2/2016

* cited by examiner

*Primary Examiner* — Don K Wong
(74) *Attorney, Agent, or Firm* — Canon U.S.A., Inc. IP Division

(57)                ABSTRACT

A radiation imaging apparatus having a function of detecting a start and an end of emission of radiation and an amount of emission of radiation includes a plurality of pixels configured to generate signals according to a dose of radiation, signal lines connected to the plurality of pixels, a reading circuit configured to read the signals from the pixels via the signal lines and generate values according to the signals, and a control unit configured to control an operation of the reading circuit. A row including a pixel from which a signal has been read during the emission of radiation is not read when a diagnosis image is generated.

11 Claims, 9 Drawing Sheets

Figure 5:
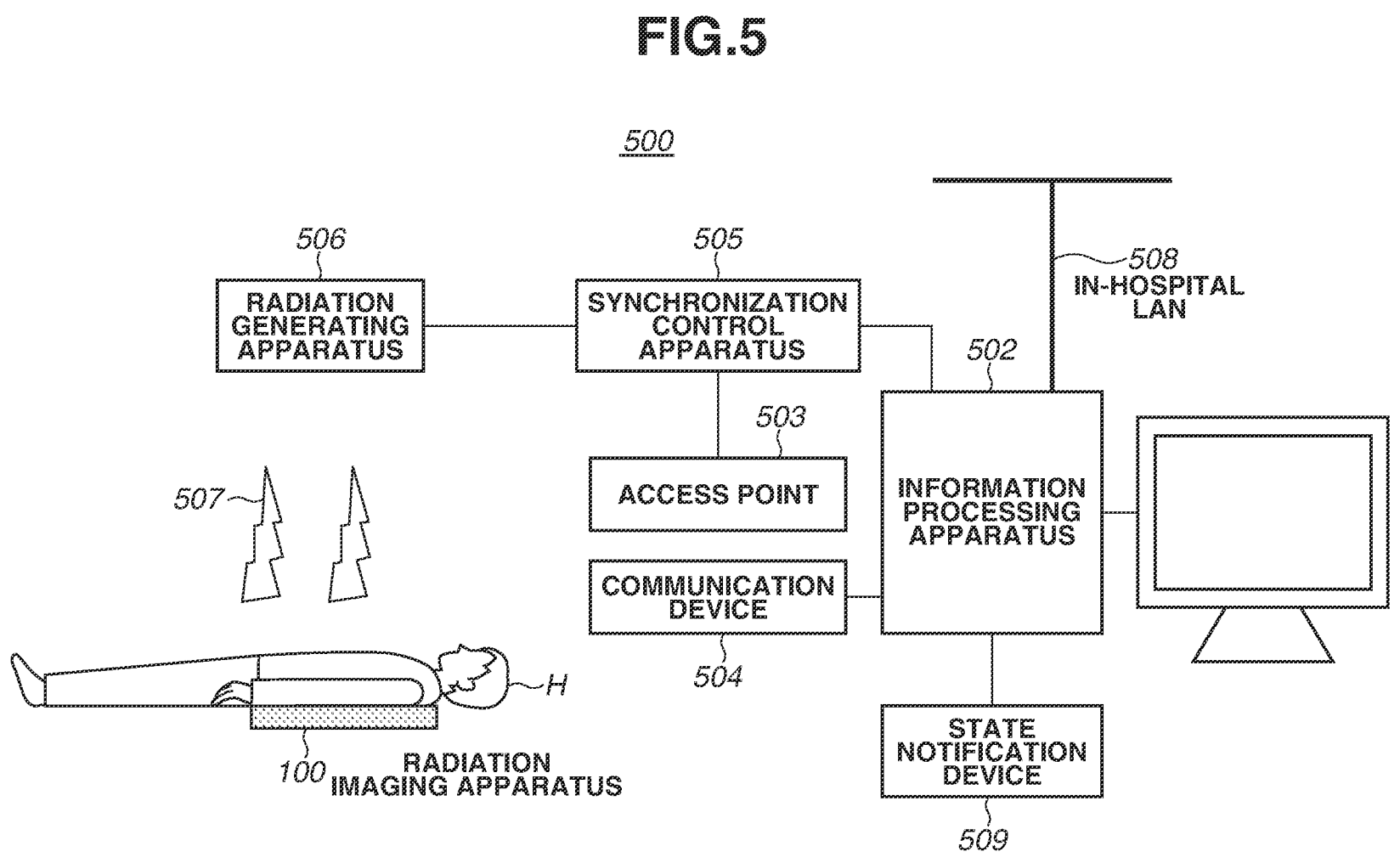

508 IN-HOSPITAL LAN

502 INFORMATION PROCESSING APPARATUS

505 SYNCHRONIZATION CONTROL APPARATUS

503 ACCESS POINT

504 COMMUNICATION DEVICE

509 STATE NOTIFICATION DEVICE

506 RADIATION GENERATING APPARATUS

507

H

100 RADIATION IMAGING APPARATUS

FIG.7

RADIATION IMAGING APPARATUS AND RADIATION IMAGING SYSTEM

BACKGROUND OF THE INVENTION

Field of the Invention

The present invention relates to a radiation imaging apparatus and a radiation imaging system.

Description of the Related Art

Radiation imaging apparatuses having an automatic exposure control (AEC) function are known. Such radiation imaging apparatuses can measure a radiation dose being emitted, and can end the emission of radiation according to a result of the measurement. For example, a radiation imaging apparatus causes only certain pixels set for radiation detection to operate at a high speed during emission of radiation to monitor a radiation dose.

As such a radiation imaging apparatus, for example, Japanese Patent Application Laid-Open No. 2016-025465 discusses a radiation imaging apparatus that continues to read charges of certain pixels set for radiation detection during emission of radiation, to control automatic exposure. After the control, the radiation imaging apparatus sequentially reads pixels for image generation to generate an image.

In the technique discussed in Japanese Patent Application Laid-Open No. 2016-025465, there is still room for improvement in image quality of radiation images that have been generated by reading signals for image generation after the automatic exposure control.

SUMMARY OF THE INVENTION

The present invention is directed to providing a high-quality radiation image. According to an aspect of the present invention, a radiation imaging apparatus includes a pixel unit including a plurality of elements arranged in a matrix and configured to generate charges based on emission of radiation, a plurality of driving lines connecting the plurality of elements in each row, and a plurality of signal lines connecting the plurality of elements in each column, a bias supply unit configured to supply a bias voltage to the plurality of elements of the pixel unit, a driving unit configured to supply a driving signal to each of the plurality of driving lines, a reading unit configured to read, via the signal lines, signals based on charges from the elements connected to the driving line to which the driving signal is supplied, an image generation unit configured to generate a radiation image based on the signals read by the reading unit, and a control unit configured to control operations of the driving unit and the reading unit, wherein in a case where the driving unit supplies a driving signal to any of the driving lines during emission of radiation, the control unit controls the driving unit to sequentially supply, after the emission of radiation, driving signals to the rest of the plurality of driving lines which are other than the any of the driving lines to which the driving signal has been supplied during the emission of radiation.

According to another aspect of the present invention, a radiation imaging system includes the radiation imaging apparatus, and a processing apparatus configured to acquire information regarding a radiation image from the radiation imaging apparatus and process the information.

Further features of the present invention will become apparent from the following description of exemplary embodiments with reference to the attached drawings.

BRIEF DESCRIPTION OF THE DRAWINGS

FIG. 5 is a diagram illustrating an example of a configuration of a radiation imaging system according to the exemplary embodiment.

FIG. 7 is a diagram illustrating relationships between the radiation imaging apparatus, a driving circuit, and a voltage according to the exemplary embodiment.

DESCRIPTION OF THE EMBODIMENTS

With reference to the attached drawings, exemplary embodiments of the present invention will be described below. Components similar throughout various exemplary embodiments are designated by the same reference signs, and are not redundantly described. The exemplary embodiments can be appropriately changed and combined together.

Figure 1:
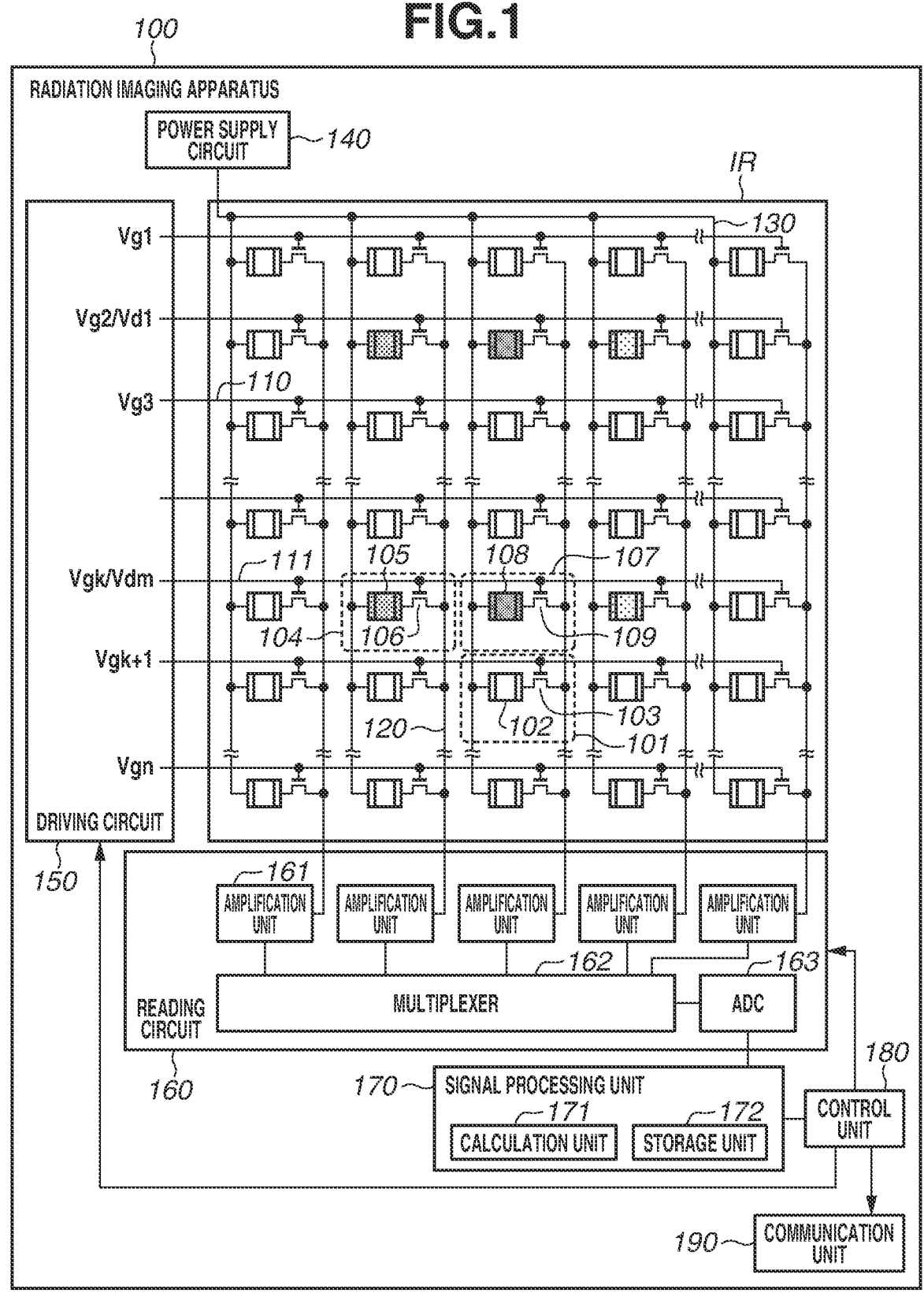
FIG. 1 is a diagram illustrating a configuration of a radiation imaging apparatus according to an exemplary embodiment.

FIG. 1 illustrates an example of a configuration of a radiation imaging apparatus 100 according to a first exemplary embodiment of the present invention. The radiation imaging apparatus 100 includes a plurality of pixels arranged in a matrix including a plurality of rows and columns in an imaging region IR, a plurality of driving lines 110, and a plurality of signal lines 120. Each of the plurality of driving lines 110 connects a plurality of pixels in a row, and corresponds to a different one of the rows of the pixels. Similarly, each of the plurality of signal lines 120 connects a plurality of pixels in a column, and corresponds to a different one of the columns of the pixels.

The plurality of pixels includes a plurality of imaging pixels 101 that is used to acquire a radiation image, one or more detection pixels 104 that are used to monitor a radiation emission amount, and one or more correction pixels 107 that are used to correct the radiation emission amount. The sensitivity of the correction pixel 107 to radiation is lower than the sensitivity of the detection pixel 104 to radiation. That is, the imaging region IR including the plurality of pixels is a sensor unit that detects radiation 507 from a radiation generating apparatus 506. The sensor unit is also referred to as a "pixel unit".

Each imaging pixel 101 includes a conversion element 102 capable of generating a charge based on emission of radiation, and a switch element 103 that connects a corresponding one of the signal lines 120 and the conversion element 102 to each other. Each of the detection pixels 104 includes a conversion element 105 that converts radiation into a charge, and a switch element 106 that connects a corresponding one of the signal line 120 and the conversion element 105 to each other. The detection pixel 104s are disposed such that the detection pixels 104 are included in rows and columns including the plurality of imaging pixels 101. Each of the correction pixels 107 includes a conversion element 108 that converts radiation into a charge, and a switch element 109 that connects a corresponding one of the signal lines 120 and the conversion element 108 to each other. The correction pixels 107 are disposed such that correction pixels 107 are included in rows and columns including the plurality of imaging pixels 101. In FIG. 1 and subsequent figures, the conversion elements 102, the conversion elements 105, and the conversion elements 108 are differently shaded to be distinguishable between the imaging pixels 101, the detection pixels 104, and the correction pixels 107.

The conversion elements 102, the conversion elements 105, and the conversion elements 108 each may include a scintillator that converts radiation into light, and a photo-electric conversion element that converts the light into an electric signal. Generally, the scintillator has a sheet-like shape to cover the imaging region IR and is shared between some pixels. Alternatively, the conversion elements 102, the conversion elements 105, and the conversion elements 108 each may include a conversion element that directly converts radiation into an electric signal.

The switch element 103, the switch element 106, and the switch element 109 each may be, for example, a semiconductor of, for example, amorphous silicon or polycrystalline silicon, including a thin-film transistor (TFT) having an active region.

A first electrode of the conversion element 102 is connected to a first main electrode of the switch element 103, and a second electrode of the conversion element 102 is connected to a bias line 130. Each bias line 130 extends in a column direction and is commonly connected to the second electrodes of a plurality of the conversion elements 102 arranged in the column direction. The bias line 130 receives a bias voltage Vs from a power supply circuit 140 as a bias supply unit. In the receiving, the power supply circuit 140 may be configured to amplify the bias voltage Vs and read the amplified bias voltage Vs. Second main electrodes of the switch elements 103 of one or more of the imaging pixels 101 included in a single column are connected to a corresponding one of the signal lines 120. Control electrodes of the switch elements 103 of one or more of the imaging pixels 101 included in a single row are connected to a corresponding one of the driving lines 110.

The detection pixels 104 and the correction pixels 107 also have a pixel configuration similar to that of the imaging pixel 101 and each are connected to a corresponding one of the driving lines 110 and a corresponding one of the signal lines 120. The detection pixels 104 and the correction pixels 107 are connected to the signal lines 120 in a mutually exclusive manner. More specifically, the correction pixels 107 are not connected to the signal lines 120 to which the detection pixels 104 are connected. The detection pixels 104 are not connected to the signal lines 120 to which the correction pixels 107 are connected. The imaging pixels 101 are connected to the signal lines 120 to which the detection pixels 104 or the correction pixels 107 are connected.

A driving circuit 150 as a driving unit is configured to supply driving signals to driving target pixels via some of the driving lines 110 according to signals from a control unit 180. In the present exemplary embodiment, the driving signals are signals for turning on the switch elements included in the driving target pixels. The switch element of each pixel is turned on in response to a high-level signal and turned off in response to a low-level signal. Thus, the "high-level signal" is referred to as a driving signal. In response to a driving signal being supplied to a pixel, a charge accumulated in the conversion element of the pixel can be read as a signal based on the charge by a reading circuit 160. In a case where a driving line 110 is connected to at least one of the detection pixel 104 and the correction pixel 107, the driving line 110 is referred to as a detection driving line 111 (see FIG. 3 described below).

The reading circuit 160 is configured to read signals from the plurality of pixels via the signal lines 120. The reading circuit 160 includes a plurality of amplification units 161, a multiplexer 162, and an analog-to-digital converter (hereinafter, "AD converter") 163. Each of the plurality of signal lines 120 is connected to a corresponding one of the amplification units 161 of the reading circuit 160. Each of the signal line 120 corresponds to a different one of the amplification units 161. The multiplexer 162 selects one of the plurality of amplification units 161 in a predetermined order and supplies signals from the selected one of the amplification units 161 to the AD converter 163. The AD converter 163 converts the supplied signals into digital signals and outputs the digital signals.

Signals read from the imaging pixels 101 are supplied to a signal processing unit 170 and subjected to a calculation process or a storage process by the signal processing unit 170. Specifically, the signal processing unit 170 includes a calculation unit 171 and a storage unit 172. Based on the signals read from the imaging pixels 101, the calculation unit 171 generates a radiation image and supplies the radiation image to the control unit 180. Thus, the signal processing unit 170 (mainly the calculation unit 171) functions as an image generation unit. Signals read from the detection pixels 104 and the correction pixels 107 are supplied to the signal processing unit 170 and subjected to a calculation process or a storage process by the calculation unit 171 of the signal processing unit 170. Specifically, based on the signals read from the detection pixels 104 and the correction pixels 107, the signal processing unit 170 outputs information indicating emission of radiation to the radiation imaging apparatus 100. For example, the signal processing unit 170 detects emission of radiation to the radiation imaging apparatus 100 and determines a radiation emission amount and/or an integrated radiation emission amount.

Based on the information from the signal processing unit 170, the control unit 180 controls the driving circuit 150 and the reading circuit 160. Based on the information from the signal processing unit 170, for example, the control unit 180 controls the start and the end of exposure (accumulation of charges corresponding to the emitted radiation in the imaging pixels 101). The control unit 180 may include a general-purpose processing circuit, such as a microprocessor, or may include a dedicated processing circuit, such as an application-specific integrated circuit (ASIC). In a case where the control unit 180 includes a general-purpose processing circuit, the control unit 180 may further include a memory.

To determine the radiation emission amount, the control unit 180 controls the driving circuit 150 to scan only the detection driving lines 111, which allows only signals from the detection pixels 104 and the correction pixels 107 to be read. More specifically, during emission of radiation, the driving circuit 150 supplies driving signals to the detection driving lines 111. Then, the control unit 180 controls the reading circuit 160 to read signals of columns corresponding to the detection pixels 104 and the correction pixels 107 and output the signals as information indicating the radiation emission amount. By the above-described operation, the radiation imaging apparatus 100 obtains emission information in the detection pixels 104 during emission of radiation.

A communication unit 190 is controlled by the control unit 180 and has a function of performing communication between the radiation imaging apparatus 100 and an external device. The communication may be performed using the communication unit 190, which achieves communication based on a desired method or standard, such as wired communication or wireless communication, and is not limited to a particular standard. To be compatible with a plurality of communication standards, a plurality of communication units 190 may be mounted.

Figure 2:
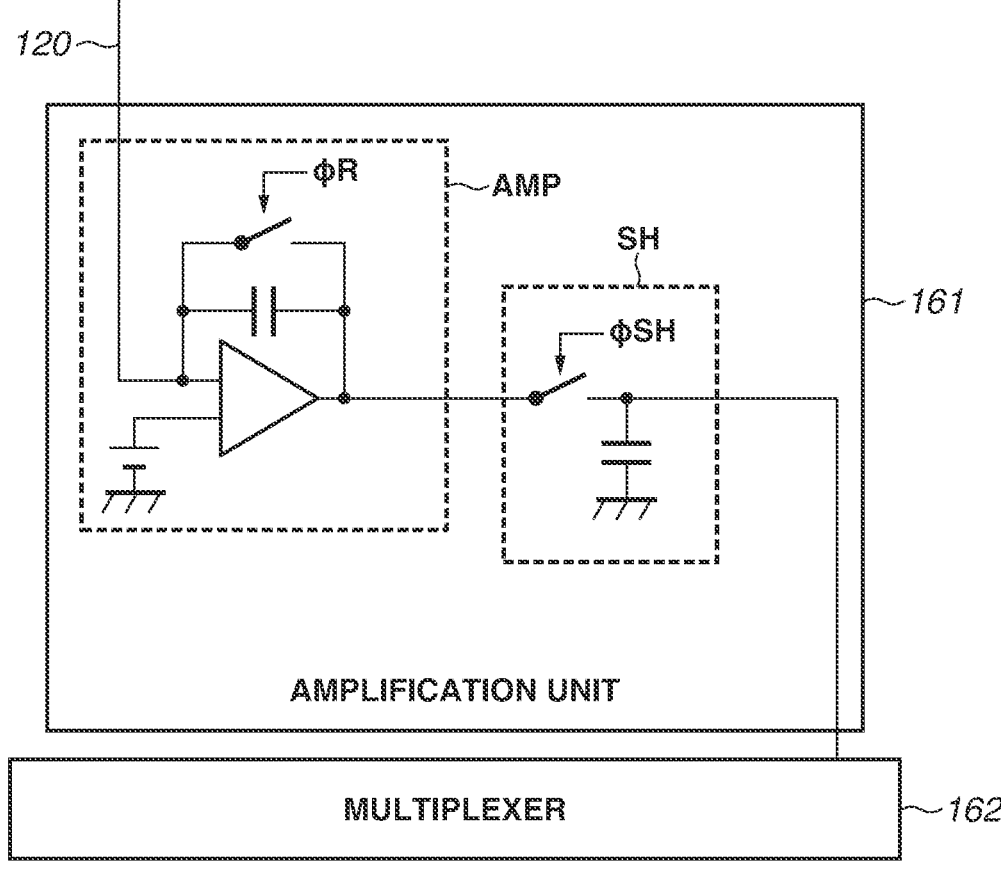
FIG. 2 is a diagram illustrating a configuration of an amplification unit according to the exemplary embodiment.

FIG. 2 illustrates an example of a detailed circuit configuration of the amplification unit 161. The amplification unit 161 includes a differential amplification circuit AMP and a sample hold circuit SH. The differential amplification circuit AMP amplifies a signal that appears in the signal line 120, and outputs the amplified signal. In response to a signal φR supplied from the control unit 180 to a switch element of the differential amplification circuit AMP, the potential of the signal line 120 is reset. An output from the differential amplification circuit AMP can be held in the sample hold circuit SH. In response to a signal φSH supplied from the control unit 180 to a switch element of the sample hold circuit SH, a signal in the sample hold circuit SH is held. The signal held in the sample hold circuit SH is read by the multiplexer 162.

Figure 3:
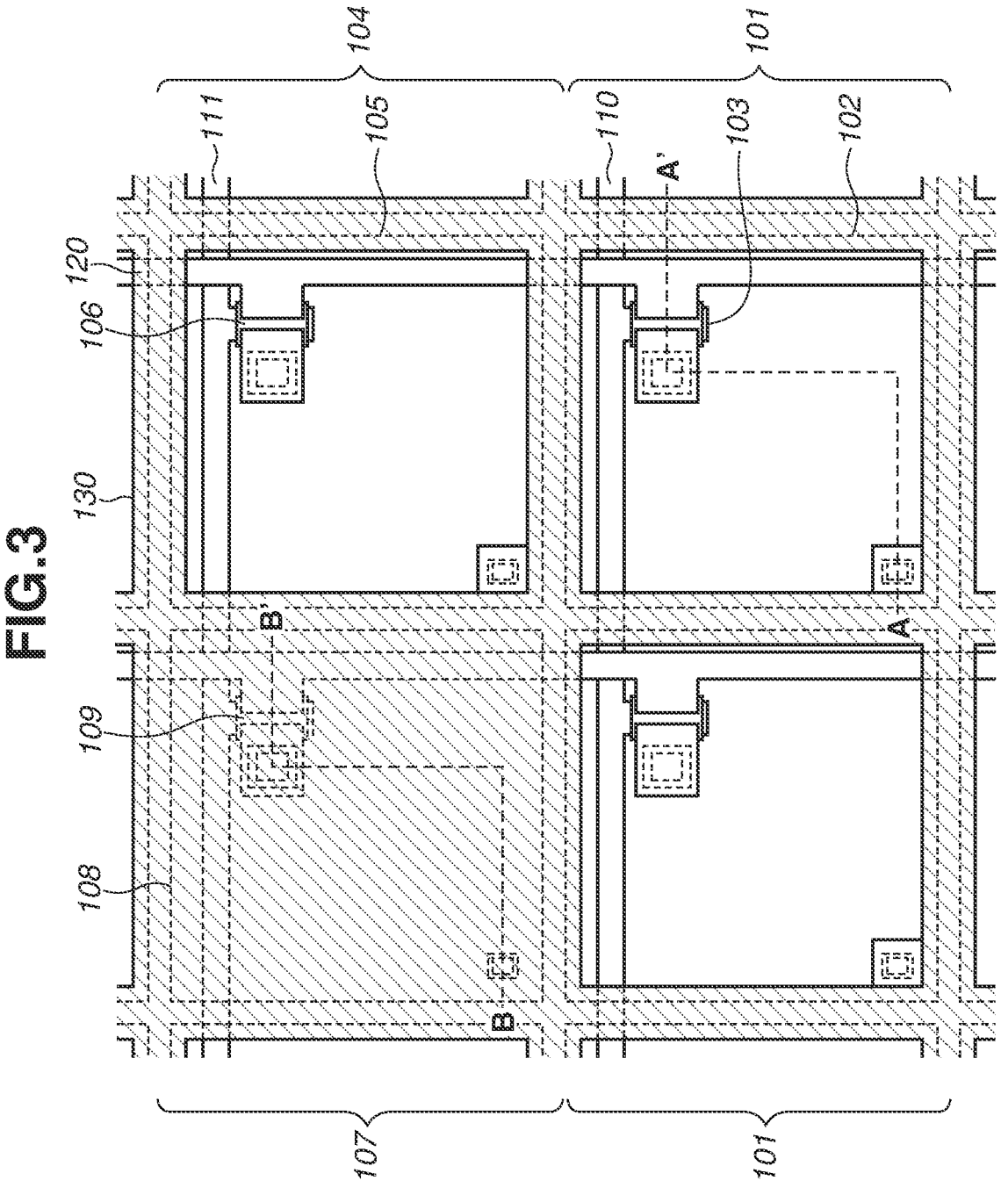
FIG. 3 is a plan view illustrating configurations of pixels according to the exemplary embodiment.
Figures 4A, 4B:
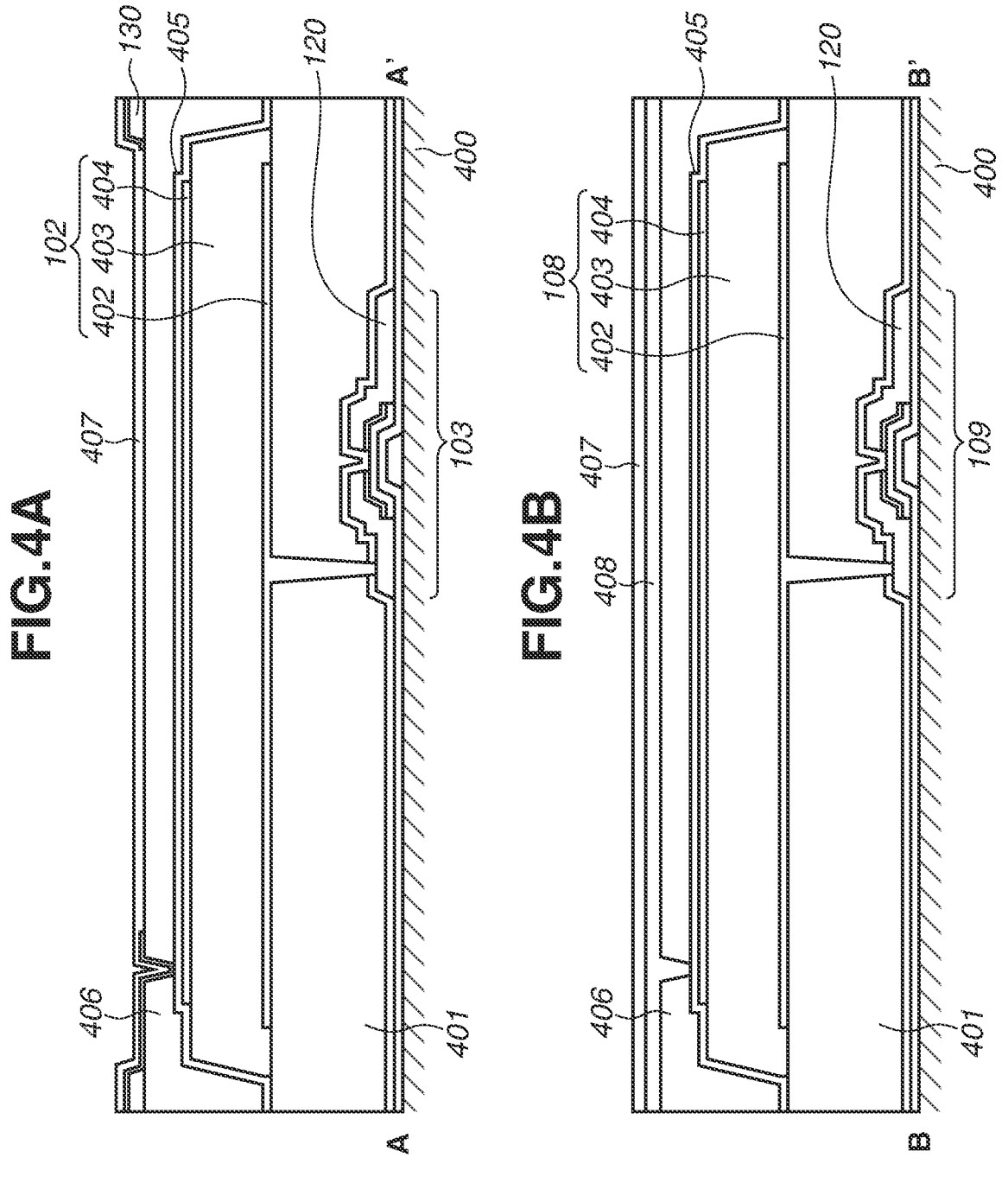
FIGS. 4A and 4B are cross-sectional views each illustrating a configuration of pixels according to the exemplary embodiment.

With reference to FIGS. 3, 4A, and 4B, an example of the structure of pixels of the radiation imaging apparatus 100 will be described. FIG. 3 is a plan view illustrating the configuration of an imaging pixel 101, a detection pixel 104, and a correction pixel 107 of the radiation imaging apparatus 100. The plan view is equivalent to an orthographic projection onto a plane parallel to the imaging region IR of the radiation imaging apparatus 100. In a hatched area in FIG. 3, a metal layer is disposed on the conversion element 108 of the correction pixel 107 and shields the conversion element 108 from light.

FIG. 4A is a cross-sectional view of the imaging pixel 101 along an A-A' line in FIG. 3. A cross-sectional view of the detection pixel 104 is similar to the cross-sectional view of the imaging pixel 101. On an insulating supporting substrate 400, which is a glass substrate, for example, the switch element 103 is disposed. The switch element 103 may be a TFT. On the switch element 103, an interlayer insulating layer 401 is disposed. Over the interlayer insulating layer 401, the conversion element 102 is disposed. The conversion element 102 is a photoelectric conversion element capable of converting light into an electric signal. For example, the conversion element 102 includes an electrode 402, a PIN photodiode 403, and an electrode 404. The conversion element 102 may include a metal-insulator-semiconductor (MIS) sensor instead of the PIN photodiode.

Over the conversion element 102, a protective film 405, an interlayer insulating layer 406, the bias line 130, and a protective film 407 are disposed in this order. On the protective film 407, a planarization film and a scintillator (not illustrated) are disposed. The electrode 404 is connected to the bias line 130 via a contact hole. The material of the electrode 404 is indium tin oxide (ITO) having light transmission properties, and the electrode 404 can transmit light converted from radiation by the scintillator (not illustrated).

FIG. 4B is a cross-sectional view of the correction pixel 107 along a B-B' line in FIG. 3. The correction pixel 107 may be similar to the imaging pixel 101 and the detection pixel 104 except that the conversion element 108 is covered by a light-blocking member 408. For example, the light-blocking member 408 is formed of a metal layer on the same layer as the bias line 130. Since the conversion element 108 of the correction pixel 107 is covered by the light-blocking member 408, sensitivity of the correction pixel 107 to radiation is significantly lower than sensitivity of the imaging pixel 101 and the detection pixel 104. It can also be said that a charge accumulated in the conversion element 108 of the correction pixel 107 is not caused by radiation.

FIG. 5 illustrates an example of a configuration of a radiation imaging system 500 including the radiation imaging apparatus 100. The radiation imaging system 500 includes the radiation imaging apparatus 100 and an information processing apparatus 502. It is desirable that the radiation imaging system 500 should include an access point 503, a communication device 504, a synchronization control apparatus 505, and the radiation generating apparatus 506.

The radiation imaging apparatus 100 captures a radiation image based on radiation 507 passing through an object H. The radiation 507 incident on the radiation imaging apparatus 100 is converted into a charge, the charge is further processed as image data, and the image data is sent to the information processing apparatus 502.

The information processing apparatus 502 is a control apparatus achieved by a known technique, such as a general-purpose computer, and includes a display unit, an input unit, and a control unit. The information processing apparatus 502 performs image processing on image data received from the radiation imaging apparatus 100 to correct, save, and display the image data. In this process, some or all the functions of the image processing may be performed by the radiation imaging apparatus 100.

The information processing apparatus 502 displays a radiation image to a user and instructs the user to capture an image through the display unit. The information processing apparatus 502 has a function of receiving an input indicating, for example, an imaging condition from the user via the input unit. The control unit of the information processing apparatus 502 has functions of comparing an acquired signal intensity and a threshold, responding to a connection request, and transmitting information for performing communication using a wireless communication unit, such as wireless information described below.

The access point 503 is a device that relays a radio wave for wirelessly exchanging information between the radiation imaging apparatus 100 and the information processing apparatus 502. In this operation, in the radiation imaging apparatus 100, the control unit 180 controls the communication unit 190 to perform wireless communication. The access point 503 is connected to the information processing apparatus 502 via the synchronization control apparatus 505 in FIG. 5, but may be directly connected to the information processing apparatus 502.

The communication device 504 is connected to the information processing apparatus 502 and serves as a device that transmits and receives a radio wave for performing wireless short-range communication between the radiation imaging apparatus 100 and the information processing apparatus 502. For example, the communication device 504 is a dongle connected to the information processing apparatus 502 via a Universal Serial Bus (USB) interface. The communication device 504 is a device compatible with at least one of the Bluetooth® Basic Rate/Enhanced Data Rate (BR/EDR) standard and the Bluetooth® Low Energy (Bluetooth® LE) standard.

The communication device 504 may be a radio-frequency identification (RFID) device that exchanges information through short-range wireless communication using an electromagnetic field and a radio wave through a tag in which identification (ID) information is embedded. The communication method of RFID may be an electromagnetic induction method or a radio wave method. The communication device 504 may have the function of an access point.

In the above description with reference to FIG. 5, an example in which the communication device 504 is connected to the information processing apparatus 502 has been described. The present invention, however, is not limited to this. The communication device 504 may be connected to another apparatus, such as the radiation generating apparatus 506, included in the radiation imaging system 500. A device built into the radiation imaging system 500 in advance may be used instead of the communication device 504.

To the information processing apparatus 502, a state notification device 509 is connected as a unit for informing the user. Based on information regarding the radiation imaging apparatus 100 received from the radiation imaging apparatus 100 via the access point 503 or received from the communication device 504, the state notification device 509 notifies the user of a current state of the radiation imaging apparatus 100 or completion of particular processing.

As the state notification device 509, a light emitter, such as a light-emitting diode (LED) is used. The state notification device 509 associates a plurality of lighting patterns with respective current states of the radiation imaging apparatus 100 in advance, to perform a notification to the user. The state notification device 509 may use a sound source, such as a loudspeaker. In this case, the state notification device 509 associates buzzer sound patterns with respective current states of the radiation imaging apparatus 100 in advance, to perform a notification to the user. Alternatively, these forms may be used in combination.

The description has been given on an example in which the state notification device 509 is connected to the information processing apparatus 502. Alternatively, a device, such as a display or a loudspeaker, included in the information processing apparatus 502 may be used instead of the state notification device 509.

The synchronization control apparatus 505 has a circuit serving as a medium of communication and monitors a state of the radiation imaging apparatus 100 and the radiation generating apparatus 506. For example, the synchronization control apparatus 505 controls emission of the radiation 507 from the radiation generating apparatus 506 and controls imaging of the object H by the radiation imaging apparatus 100. The synchronization control apparatus 505 may have a built-in hub for connecting a plurality of network devices.

To generate the radiation 507, such as an X-ray, the radiation generating apparatus 506 includes a radiation tube that accelerates an electron at a high voltage, to bring the electron into collision with an anode, for example. An example of the radiation 507 is, typically, an X-ray, but an α-ray, a β-ray, a γ-ray, or a neutron ray may be used.

An in-hospital local area network (LAN) 508 is a local area network constructed in a hospital and has a function of transmitting and receiving a radiation image captured by the radiation imaging system 500 to and from various quarters in the hospital.

In the radiation imaging system 500 illustrated in FIG. 5, the radiation 507 emitted from the radiation generating apparatus 506 is emitted to the object H which is a patient. The radiation imaging apparatus 100 generates a radiation image based on the radiation 507 passing through the object H.

The radiation imaging system 500 can perform imaging by synchronous imaging and asynchronous imaging. The synchronous imaging refers to an imaging method in which an electrical synchronization signal is exchanged between the radiation imaging apparatus 100 and the radiation generating apparatus 506 via the synchronization control apparatus 505, to synchronize a timing of emission of the radiation 507 and a timing of imaging.

On the other hand, the asynchronous imaging refers to an imaging method in which an electrical synchronization signal is not exchanged between the radiation imaging apparatus 100 and the radiation generating apparatus 506, and imaging is started in response to entrance of the radiation 507 detected by the radiation imaging apparatus 100. In the asynchronous imaging, the radiation imaging apparatus 100 may transfer a radiation image every time imaging is performed, or may store a captured image inside the radiation imaging apparatus 100 every time imaging is performed without transferring the captured image.

The radiation imaging system 500 can perform imaging under imaging conditions for generally performing imaging in radiation imaging, such as fluoroscopic imaging, continuous imaging, still image capturing, digital subtraction angiography (DSA) imaging, roadmap imaging, program imaging, tomographic imaging, and tomosynthesis imaging.

In the radiation imaging system 500, settings for various functions, such as an imaging frame rate setting, a tube voltage setting, a tube current setting, a sensor reading area setting, a sensor driving binning setting, a collimator aperture setting, a radiation window width setting, and a setting regarding whether to capture a radiation image and store the radiation image in the radiation imaging apparatus 100, are performed. Additionally, in the radiation imaging system 500, settings for functions of automatic dose control (ADC) and automatic exposure control (AEC) are performed.

To the information processing apparatus 502, a dose, an emission upper limit time (ms), a tube current (mA), a tube voltage (kV), and a region of interest (ROI) as a region where the radiation 507 should be monitored are input via the input unit in the information processing apparatus 502. In a case where an exposure switch included in the radiation generating apparatus 506 is operated, the information processing apparatus 502 transmits a start request signal to the radiation imaging apparatus 100. The start request signal is a signal requesting the start of emission of the radiation 507. In response to receipt of the start request signal, the radiation imaging apparatus 100 starts preparation to receive emission of the radiation 507. After completion of the preparation, the radiation imaging apparatus 100 transmits a ready-for-start signal to the radiation generating apparatus 506 via the access point 503 or the communication device 504. The ready-for-start signal is a signal notifying that emission of the radiation 507 can be started. In response to receipt of the ready-for-start signal, the radiation generating apparatus 506 starts emitting the radiation 507.

In a case where the radiation 507 being emitted reaches a threshold of an integrated value of a dose of the radiation 507, the radiation imaging apparatus 100 transmits an emission stop signal to the radiation generating apparatus 506 via the access point 503 or the communication device 504. The emission stop signal is a signal requesting the end of the emission of the radiation 507. In response to receipt of the emission stop signal, the radiation generating apparatus 506 ends the emission of the radiation 507. The threshold of the dose is determined by, for example, the control unit 180, based on an input value of the dose, emission intensity of the radiation 507, and communication delay and processing delay between units. In a case where an emission time of the radiation 507 reaches an input emission upper limit time, and even in a case where the emission stop signal is not received, the radiation generating apparatus 506 may stop emitting the radiation 507.

After the emission of the radiation 507 (after the emission is stopped), the control unit 180 of the radiation imaging apparatus 100 performs control to sequentially supply driving signals to the driving lines 110 to which only the imaging pixels 101 are connected (the driving lines 110 other than the detection driving lines 111). By this processing, the reading circuit 160 reads image signals of the imaging pixels 101 and acquires a radiation image. Charges accumulated in the detection pixels 104 have been read during the emission of the radiation 507, and since the correction pixels 107 are shielded from light, signals from these pixels cannot be used to form the radiation image. Thus, the signal processing unit 170 of the radiation imaging apparatus 100 performs an interpolation process using pixel values of imaging pixels 101 in the vicinity of the detection pixels 104 and the correction pixels 107, to interpolate pixel values at the positions of the detection pixels 104 and the correction pixels 107. That is, the signal processing unit 170 performs signal interpolation for elements (pixels) connected to the driving lines 110 to which driving signals have been supplied during the emission of the radiation 507, and generates the radiation image.

Figure 6:
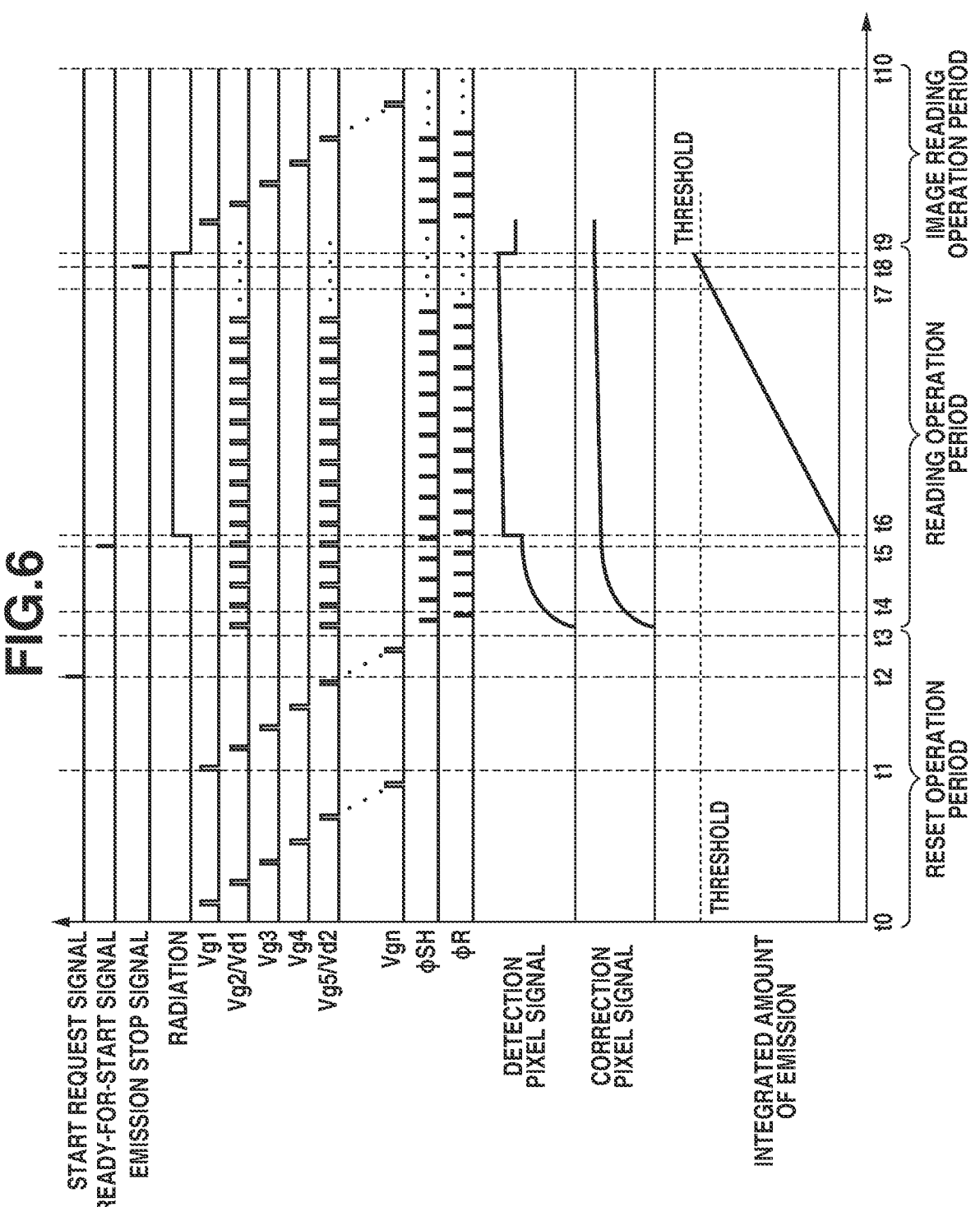
FIG. 6 is a diagram illustrating an example of an operation of the radiation imaging system according to the exemplary embodiment.

With reference to FIG. 6, an example of the operation of the radiation imaging apparatus 100 is described. This operation is executed by cooperation between the control unit 180, which controls the driving circuit 150 and the reading circuit 160, and the signal processing unit 170. By the operation, the amount of radiation emitted to the radiation imaging apparatus 100 is determined.

In FIG. 6, an item "RADIATION" shows whether radiation is emitted to the radiation imaging apparatus 100. A low level indicates that radiation is not emitted, and a high level indicates that radiation is emitted.

Items from "Vg1" to "Vgn" show driving signals that is supplied from the driving circuit 150 to the plurality of driving lines 110. The driving signal "Vgn" is a signal that is supplied to a driving line 110 in an n-th row (n=1, . . . , the total number of driving lines). As described above, some of the plurality of driving lines 110 are also referred to as the "detection driving lines 111". A driving signal "Vdj" is a signal that is supplied to a j-th detection driving line 111 (j=1, . . . , the total number of detection driving lines).

An item indicated with the signal "φSH" shows a level of a signal that is supplied to the sample hold circuit SH of each amplification unit 161. An item indicated with the signal "OR" shows a level of a signal that is supplied to a differential amplification circuit AMP of the amplification unit 161. An item "DETECTION PIXEL SIGNAL" shows the value of a signal read from the detection pixel 104. An item "CORRECTION PIXEL SIGNAL" shows the value of a signal read from the correction pixel 107. An item "INTEGRATED AMOUNT OF EMISSION" shows the integrated value of radiation emitted to the radiation imaging apparatus 100. A method for determining the integrated value will be described below.

At a time t0, the control unit 180 starts performing a reset operation on the plurality of pixels. The "reset operation" refers to an operation of removing charges accumulated in the conversion elements of pixels, and specifically, refers to an operation of bringing the switch elements of the pixels into a conducting state by supplying a driving signal to the driving line 110. The control unit 180 controls the driving circuit 150 to reset the pixels connected to the driving line 110 in the first row.

Next, the control unit 180 resets the pixels connected to the driving line 110 in the second row.

The control unit 180 repeats the above-described operation up to the driving line 110 in the last row. At a time t1, after completion of the reset operation performed on the driving line 110 up to the last row, the control unit 180 repeats the reset operation again from the driving line 110 in the first row. This reset operation is executed by the driving circuit 150 supplying driving signals to the driving lines 110 in accordance with an instruction from the control unit 180 before emission of radiation.

At a time t2, the control unit 180 receives a start request signal from the information processing apparatus 502. In response to receipt of the start request signal, the control unit 180 performs the reset operation up to the last row and ends the reset operation. Before performing the reset operation to the last row, the control unit 180 may end the reset operation and proceed to the next processing.

For example, in a case where the control unit 180 receives the start request signal during the reset operation performed on the driving line 110 in a k-th row, the control unit 180 may advance to the next processing without performing the reset operation on the driving lines 110 in k+1-th and subsequent rows. In this case, driving for acquiring a radiation image may be adjusted, or image processing may be performed on the radiation image, to reduce a difference in level that can occur in the radiation image.

At a time t3, the control unit 180 starts a determination operation to determine the amount of radiation that is being emitted to the radiation imaging apparatus 100. In the determination operation, the control unit 180 repeatedly executes the reading operation to read signals from the detection pixels 104 and the correction pixels 107. Among the reading operations performed multiple times, one or more of the reading operations in the first half is performed to determine correction values, and the reading operations repeated in the second half is performed to continuously determine the amount of radiation at each time.

The reading operation is executed on the detection driving lines 111 and is not executed on the driving lines 110 other than the detection driving lines 111. Specifically, the driving circuit 150 supplies a driving signal to the driving line 110 that is connected to at least one of the detection pixel 104 and the correction pixel 107 (i.e., a detection driving line 111) among the plurality of driving lines 110.

Meanwhile, the driving circuit 150 does not supply a driving signal to the driving line 110 that is connected to neither the detection pixel 104 nor the correction pixel 107 among the plurality of driving lines 110. The driving circuit 150 simultaneously supplies driving signals to the driving lines 110 that are connected to at least one of the detection pixel 104 and the correction pixel 107 among the plurality of driving lines 110. Consequently, signals from a plurality of pixels connected to the same signal line 120 are read together by the reading circuit 160. Since the detection pixels 104 and the correction pixels 107 are connected to the signal lines 120 in a mutually exclusive manner, the reading circuit 160 can separately read signals of the pixels different in sensitivity from each other.

In a single execution of the reading operation, the control unit 180 performs the operation from the time t3 to a time t4. Specifically, the control unit 180 temporarily supplies driving signals to one or more detection driving lines 111. Then, the control unit 180 temporarily sets the signal φSH to a high level to hold signals read from the pixels via the signal lines 120 by the reading circuit 160 in the sample hold circuits SH.

Then, the control unit 180 temporarily sets the signal φR to a high level to reset the reading circuit 160 (specifically, the differential amplification circuits AMP of the amplification units 161 of the reading circuit 160). In a case where a region of interest is set in the imaging region IR, any signal outside the region of interest may not need to be read from the detection pixel 104.

To determine correction values, the control unit 180 performs the reading operation a predetermined number of times which is one or more times.

The signal processing unit 170 determines a correction value Od based on signals that have been read from the detection pixels 104 by the reading operation performed the predetermined number of times, and a correction value Oc based on signals that have been read from the correction pixels 107 by the reading operation performed the predetermined number of times.

The determination of the correction value Od is described in detail. In a case where the predetermined number of times is once, a single signal is read from the detection pixels 104. Thus, the signal processing unit 170 sets the value of the signal as the correction value Od. In a case where the predetermined number of times is multiple times, the signal processing unit 170 sets an average value of a plurality of read signals as the correction value Od. Instead of the average value, another statistical value may be used. Similarly, the correction value Oc is also determined based on signals read from the correction pixels 107. The signal processing unit 170 stores the determined correction values Od and Oc in the storage unit 172 so that the correction values Od and Oc can be used in subsequent processing.

After completion of the reading operation performed one or more times, then at a time t5, the control unit 180 transmits a ready-for-start signal to the radiation generating apparatus 506. The determinations of the correction values Od and Oc may be performed before or after the transmission of the ready-for-start signal. After transmission of the ready-for-start signal, the control unit 180 repeatedly executes the above-described reading operation. Every time the reading operation is performed, the signal processing unit 170 measures an amount of emission dose of radiation and determines whether the integrated value of the amount of emission dose exceeds a threshold. After the time t5, then at a time t6, emission of radiation is started. The control unit 180 controls the driving circuit 150 to cause driving signals to be supplied to the detection driving lines 111 during the emission of radiation.

In a case where the integrated amount of emission reaches a threshold, which is at a time t8, the control unit 180 transmits an emission stop signal to the synchronization control apparatus 505. The synchronization control apparatus 505 receives the emission stop signal and controls the radiation generating apparatus 506 to stop the emission of radiation.

Instead of transmission of the emission stop signal at the time t8, the control unit 180 may estimate the time t8 when the integrated amount of emission is to reach the threshold, and transmit the emission stop signal in advance. Further, the control unit 180 may obtain an estimated transmission time t7 which is obtained by factoring in a communication delay time until the signal reaches the synchronization control apparatus 505 from the communication unit 190 with respect to the predicted reach time, and transmit the emission stop signal at the estimated transmission time t7. At a time t9, in response to the control for stopping the emission performed by the synchronization control apparatus 505, the radiation generating apparatus 506 ends the emission of radiation.

After the end of the emission of radiation at the time t9, the control unit 180 reads the plurality of pixels by a time t10 and generates an image. As a general technique, the control unit 180 sequentially reads pixels corresponding to the driving signals Vg1 to Vgn as in the image reading operation period.

Figure 7:
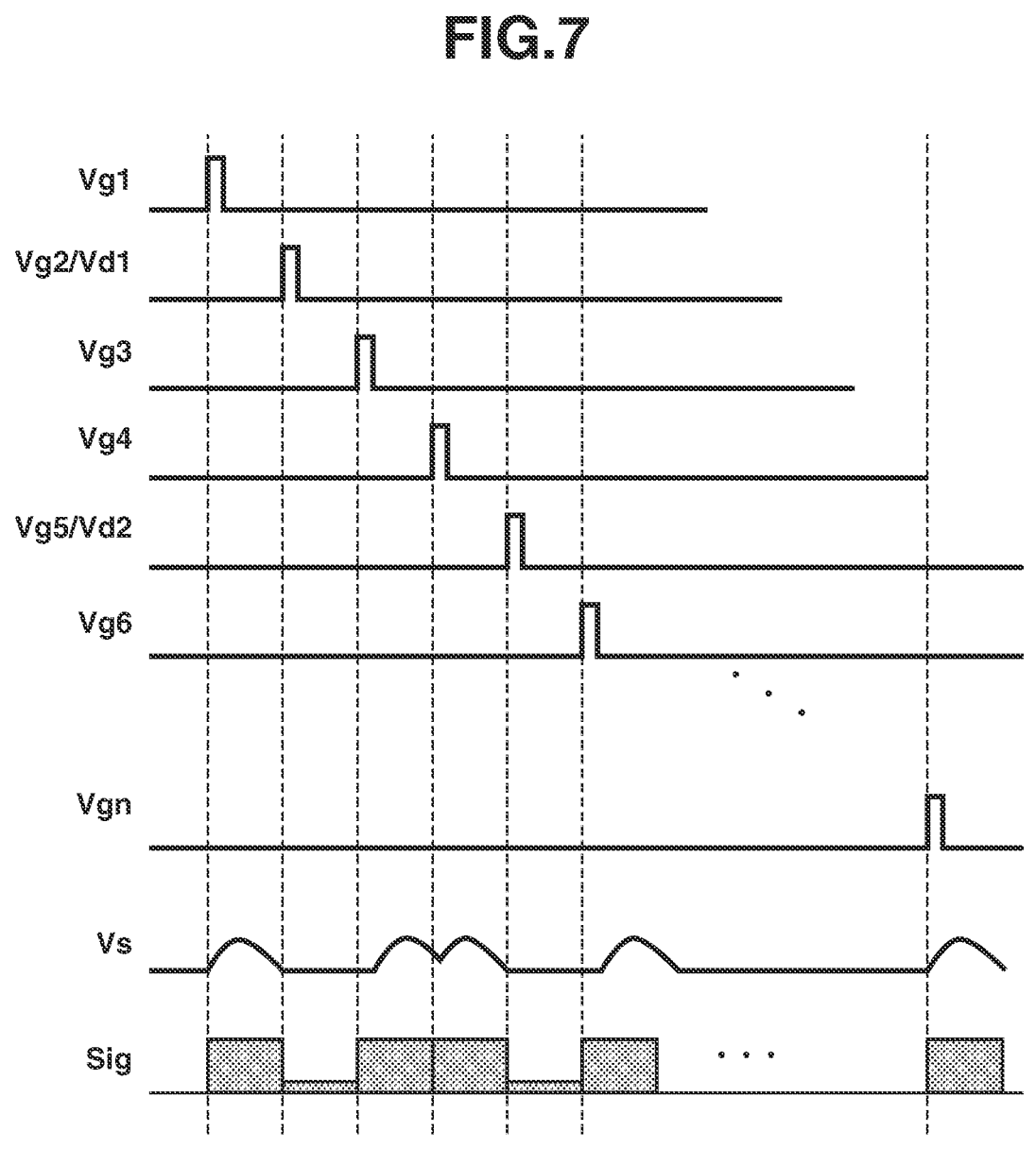

Next, with reference to FIG. 7, a description is given of a conventional reading method which is performed after the end of the emission of radiation, and an issue that can arise in the process. In FIG. 7, the driving signal Vgn is a driving signal that is supplied to the driving line 110 connected to a general pixel (pixel 101). The driving signal Vdj is a driving signal that is supplied to the detection driving line 111 connected to the detection pixel 104 or the correction pixel 107 disposed for AEC driving. The bias voltage Vs is a voltage that is supplied to the bias lines 130 connected to all the pixels.

An output Sig is an output of the signal line 120 connected to a certain amplification unit 161. FIG. 7 illustrates the general operations of these signals. In generation of a general diagnosis image (radiation image), the driving signals Vg1 to Vgn are sequentially supplied as illustrated in FIG. 7.

Since the bias voltage Vs is connected to the pixels, the bias voltage Vs is influenced in reading of image signals from the pixels. The degree of the influence differs in accordance with the amount of charge of the read image signal. In AEC driving, as illustrated in FIG. 6, since the signal Vdj is applied to a detection driving line 111 before a diagnosis image is generated to read an image signal of the driving signal Vdj, the output Sig in the AEC driving is small, and the influence on the bias voltage Vs in the AEC driving is also small. The bias voltage Vs is supplied to all the pixels and therefore changes under the influence of any output Sig, and the change in the bias voltage Vs continuously influences the output Sig of another (the next) pixel to be subsequently read. Based on this, it has been found that, for example, the output Sig output when the driving line 110 subsequent to the driving line 110 corresponding to the driving signal Vdj is driven is different from the output Sig output when the driving lines 110 corresponding to the driving signals Vgn are continuously driven, in image signal characteristics such as occurrence of phase delay or variations in maximum values, which results in occurrence of an artifact.

Figure 8:
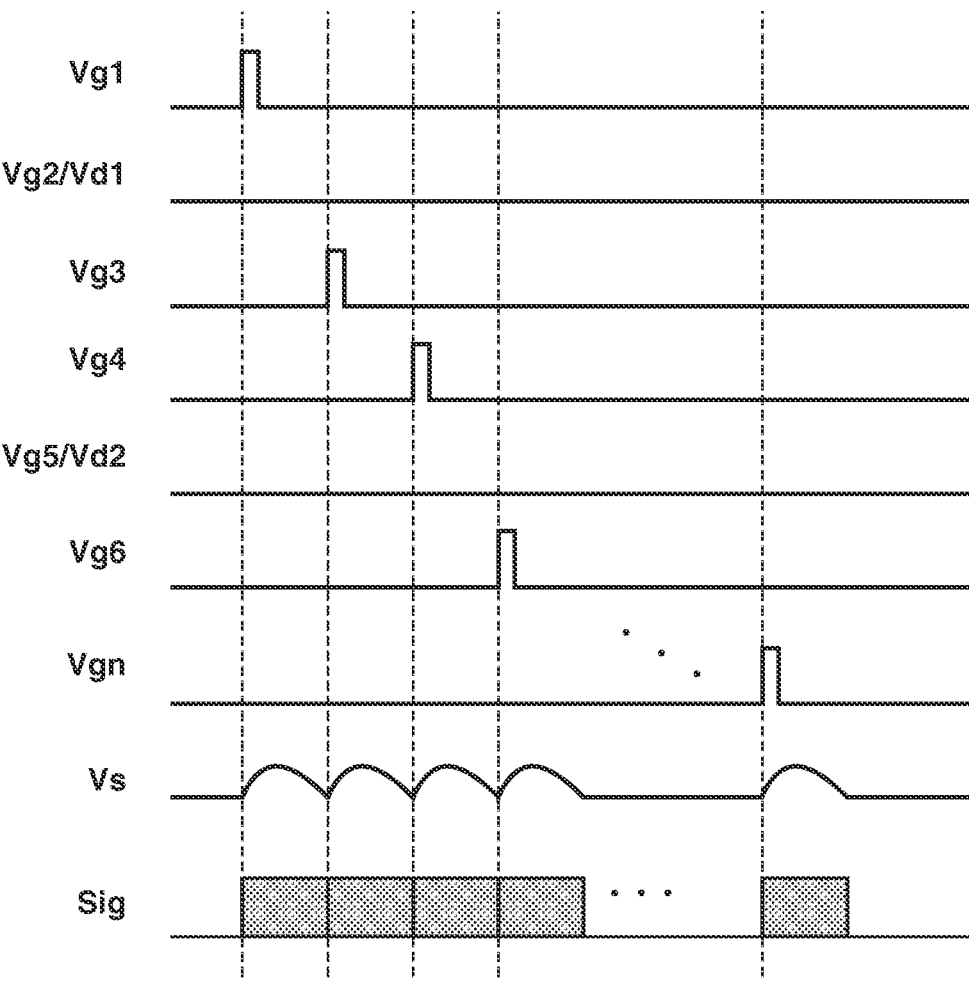
FIG. 8 is a diagram illustrating relationships between the radiation imaging apparatus, the driving circuit, and the voltage according to the exemplary embodiment.

With reference to FIG. 8, a description is given of a technique according to the present invention that addresses the issue. While, in FIG. 7, pixels corresponding to the driving signals Vgn are sequentially read, the driving signal Vdj is not supplied to the detection driving lines 111 in FIG. 8. That is, the reading operation to generate a radiation image is not performed.

At the timing when a pixel corresponding to the driving signal Vg2/Vd1 is read in FIG. 7, the driving signal Vg3 is supplied to the driving line 110 in the technique illustrated in FIG. 8. In other words, the reading operation is not performed on the pixel corresponding to the driving signal Vg2/Vd1, and the reading of the pixel is skipped. With this configuration, a row in which the amount of read charge is extremely small is omitted, and the output Sig shows similar responses to all read pixels. Thus, the image signal characteristics are stabilized. Also, in a case where the reading operation for correcting a read image signal is subsequently performed, as described above, driving signals are supplied while skipping the detection driving lines 111 to which the detection pixels 104 or the correction pixels 107 are connected, which also improves the accuracy of image signal correction. As described above, after the end of the emission of radiation and in the state where radiation is not emitted, driving signals are sequentially supplied to the rest of driving lines which are other than the driving lines to which driving signals have been supplied during the emission of radiation, whereby an excellent image can be obtained. This driving control is referred to as "first control". After the first control and in the state where radiation is not emitted, driving signals may be sequentially supplied to the rest of driving lines. With this configuration, the accuracy of image signal correction improves, whereby a more excellent radiation image can be obtained. A similar issue can also occur with a defect caused by a difference (drop) between an output value of a particular row line and an output value of other row lines due to a manufacturing flaw of a sensor (a horizontal line defect). Thus, a row to be skipped may be specified according to the number of defects or a response from the bias voltage Vs. Further, in a case where an image (the output value) of pixels corresponding to the driving signal Vdj is to be used for signal processing, pixels corresponding to the driving signals Vg1 to Vgn are read, and then, pixels corresponding to the driving signals Vd1 to Vdj are read (subjected to the reading operation), which makes uniform the image characteristics of the pixels corresponding to the driving signal Vdj. Row information regarding a row from which reading is not actually performed may be filled with a value of 0 in generation of a diagnosis image, or the row information may be estimated from the output values of image rows (close rows) before and after the row from which reading is not actually performed, and may be corrected (interpolated). In FIG. 6, the case where the AEC function operates has been described. The present invention, however, is not limited to this. This technique is effective, for example, also when the reading operation for a radiation image is performed after a case where the operation of starting or ending radiation or detecting dose information.

Figure 9:
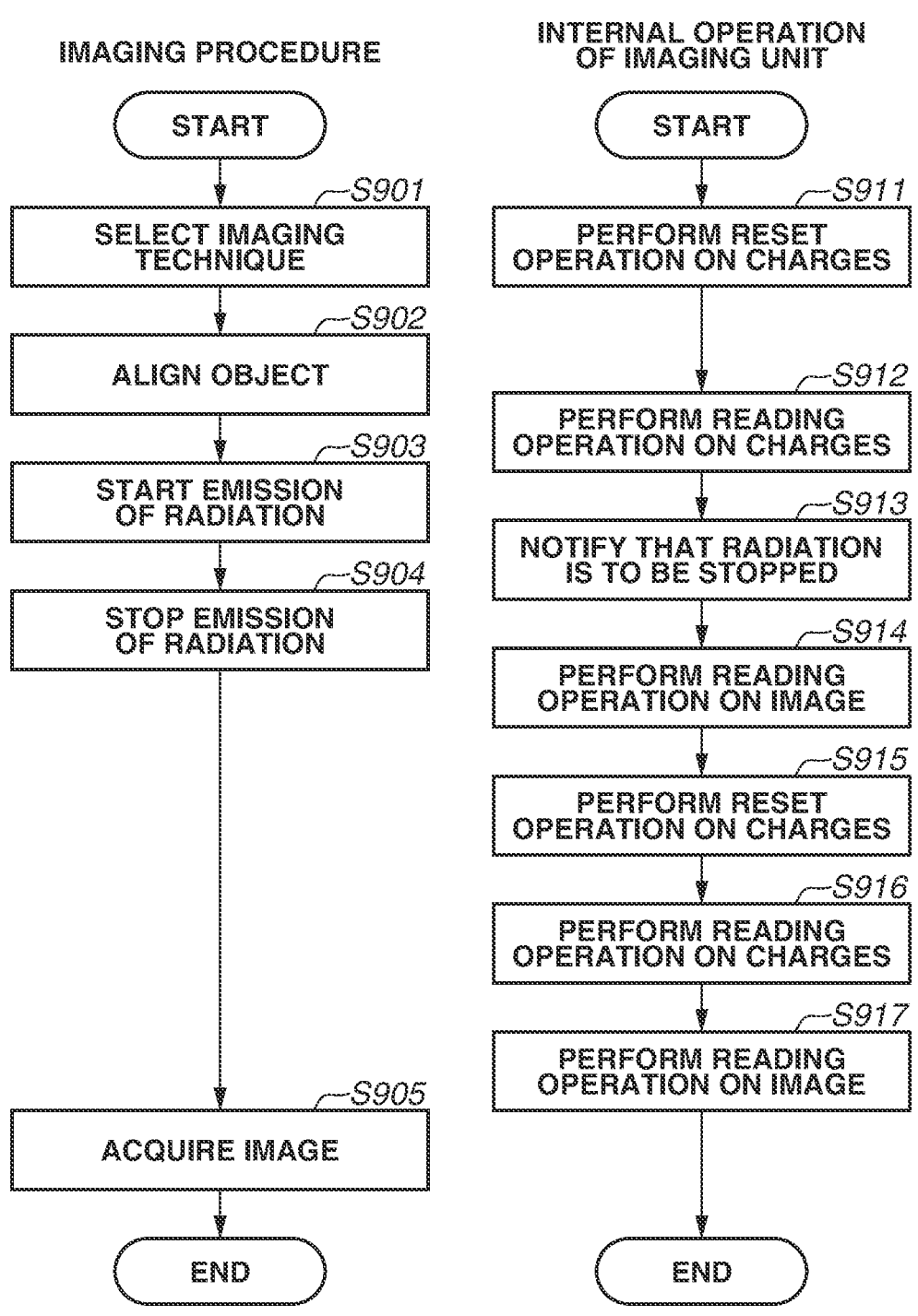
FIG. 9 is a diagram illustrating a procedure sequence of imaging and an internal operation of the radiation imaging apparatus in the imaging according to the exemplary embodiment.

With reference to FIG. 9, a description will be given of the procedure of imaging and the internal operation of an imaging unit in the imaging. In step S901, an imaging technique is selected using the information processing apparatus 502. Next, in step S902, a radiation tubular lamp, the object H, and the radiation imaging apparatus 100 are aligned. In step S912, reading of charges is started and completed by the time when emission of radiation is started. Before step S911, correction information to be used for correcting charges read in step S912 is acquired, and the charges are corrected using the acquired information, whereby the accuracy of correcting an image signal can be improved.

In step S903, emission of radiation is started. As a result, the amount of charge read by reading the charges in step S912 increases. In a case where charges greater than or equal to a certain amount are read, in step S913, a notification that the radiation is to be stopped is issued. In step S904, according to the reception of the notification that the radiation is to be stopped, the radiation is stopped. Then, in step S914, a radiation image is read.

Then, in step S915, the charges are reset to correct the radiation image read in step S914. In step S916, the reading operation for reading the charges is performed. Then, in step S917, the reading operation for reading the image is performed again. An image obtained by correcting the image in these reading operations is transferred to the information processing apparatus 502 through wired or wireless communication. In step S905, acquisition of the image is completed. The image used in the correction may be prepared in advance. In the reset operation performed on the charges in step S911, discarding charges read from the detection driving line 111 corresponding to the driving signal Vdj leads to further improvement in the accuracy of the AEC operation in step S912. In the reset of the charges in step S915, performing a reading operation similar to that in step S911 leads to further increase in image correction accuracy.

Based on the present invention, an artifact when an image is read after AEC can be reduced or prevented.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc™ (BD)), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2023-010854, filed Jan. 27, 2023, which is hereby incorporated by reference herein in its entirety.

What is claimed is:

1. A radiation imaging apparatus comprising:
a pixel unit including a plurality of elements arranged in a matrix and configured to generate charges based on emission of radiation, a plurality of driving lines connecting the plurality of elements in each row, and a plurality of signal lines connecting the plurality of elements in each column;

a bias supply unit configured to supply a bias voltage to the plurality of elements of the pixel unit;

a driving unit configured to supply a driving signal to each of the plurality of driving lines;

a reading unit configured to read, via the signal lines, signals based on charges from the elements connected to the driving line to which the driving signal is supplied;

an image generation unit configured to generate a radiation image based on the signals read by the reading unit; and a control unit configured to control operations of the driving unit and the reading unit, wherein in a case where the driving unit supplies a driving signal to any of the driving lines during emission of radiation, the control unit controls the driving unit to sequentially supply, after the emission of radiation, driving signals to the rest of the plurality of driving lines which are other than the any of the driving lines to which the driving signal has been supplied during the emission of radiation.

2. The radiation imaging apparatus according to claim 1, wherein after an end of the emission of radiation and in a state where radiation is not emitted, the control unit performs first control for controlling the driving unit to sequentially supply driving signals to the rest of the plurality of driving lines which are other than the any of the driving lines to which the driving signal has been supplied during the emission of radiation.

3. The radiation imaging apparatus according to claim 2, wherein after the first control and in the state where radiation is not emitted, the control unit performs second control for controlling the driving unit to sequentially supply driving signals to the rest of the plurality of driving lines.

4. The radiation imaging apparatus according to claim 1, wherein the control unit controls the driving unit to cause the driving unit to supply the driving signal to the driving lines before the emission of radiation, to perform a reset operation for resetting of the charges of the elements.

5. The radiation imaging apparatus according to claim 1, wherein based on signals read by the reading unit from the elements connected to the rest of the plurality of driving lines, the image generation unit interpolates the signals regarding the elements connected to the any of the driving lines to which the driving signal has been supplied during the emission of radiation, to generate a radiation image.

6. The radiation imaging apparatus according to claim 2, wherein the control unit holds information regarding a position of the driving line to which an element having a defect is connected among the plurality of elements arranged in the matrix, and in the first control, the control unit controls the driving unit to sequentially supply driving signals to the rest of the plurality of driving lines which are other than the driving line to which the driving signal has been supplied during the emission of radiation and the driving line to which the element having the defect is connected.

7. A radiation imaging system comprising:

a radiation imaging apparatus comprising:

a pixel unit including a plurality of elements arranged in a matrix and configured to generate charges based on emission of radiation, a plurality of driving lines connecting the plurality of elements in each row, and a plurality of signal lines connecting the plurality of elements in each column;

a bias supply unit configured to supply a bias voltage to the plurality of elements of the pixel unit;

a driving unit configured to supply a driving signal to each of the plurality of driving lines;

a reading unit configured to read, via the signal lines, signals based on charges from the elements connected to the driving line to which the driving signal is supplied;

an image generation unit configured to generate a radiation image based on the signals read by the reading unit; and a control unit configured to control operations of the driving unit and the reading unit, wherein in a case where the driving unit supplies a driving signal to any of the driving lines during emission of radiation, the control unit controls the driving unit to sequentially supply, after the emission of radiation, driving signals to the rest of the plurality of driving lines which are other than the any of the driving lines to which the driving signal has been supplied during the emission of radiation; and a processing apparatus configured to acquire information regarding a radiation image from the radiation imaging apparatus and process the information.

8. A radiation imaging apparatus comprising:

a plurality of pixels each including a conversion element configured to generate charges based on emission of radiation and a switching element connected to the conversion element;

a plurality of driving lines configured to connect switching elements of the plurality of pixels in each row;

a plurality of signal lines configured to connect the switching elements of the plurality of pixels in each column;

a bias supply unit configured to supply a bias voltage to conversion elements of the plurality of pixels;

a driving unit configured to supply a driving signal to each of the plurality of driving lines;

a reading unit configured to read, via the signal lines, signals based on charges from the pixels connected to a driving line to which the driving signal is supplied;

an image generation unit configured to generate a radiation image based on the signals read by the reading unit; and a control unit configured to control operations of the driving unit and the reading unit, wherein the plurality of pixels includes imaging pixels and correction pixels, and the plurality of driving lines includes a first driving line configured to connect the imaging pixels in each row and a second driving line configured to connect the imaging pixels and the correction pixels in each row, and wherein in a case where the driving unit supplies a driving signal to the second driving line during emission of radiation, the control unit controls the driving unit to sequentially supply, after the emission of radiation, the driving signal to the remaining first driving line except for the second driving line to which the driving signal has been supplied during the emission of radiation.

9. A radiation imaging system comprising:

the radiation imaging apparatus according to claim 8; and a processing apparatus configured to acquire information regarding a radiation image from the radiation imaging apparatus and process the information.

10. A radiation imaging apparatus comprising:

a plurality of pixels each including a conversion element configured to generate charges based on emission of radiation and a switching element connected to the conversion element;

a plurality of driving lines configured to connect switching elements of the plurality of pixels in each row;

a plurality of signal lines configured to connect the switching elements of the plurality of pixels in each column;

a bias supply unit configured to supply a bias voltage to conversion elements of the plurality of pixels;

a driving unit configured to supply a driving signal to each of the plurality of driving lines;

a reading unit configured to read, via the signal lines, signals based on charges from the pixels connected to a driving line to which the driving signal is supplied;

an image generation unit configured to generate a radiation image based on the signals read by the reading unit; and a control unit configured to control operations of the driving unit and the reading unit, wherein the plurality of pixels includes imaging pixels and correction pixels, and the plurality of driving lines includes first driving lines configured to connect the imaging pixels in each row and a second driving line configured to connect the imaging pixels and the correction pixels in each row, and wherein the control unit controls the driving unit to perform a first operation to sequentially supply the driving signals to the first driving lines, and the image generation unit generates a radiation image based on the signals read by the reading unit by the first operation by the driving unit.

11. A radiation imaging system comprising:

the radiation imaging apparatus according to claim 10; and a processing apparatus configured to acquire information regarding a radiation image from the radiation imaging apparatus and process the information.

*   *   *   *   *